United States Patent
Sturgis et al.

(10) Patent No.: US 12,109,282 B2
(45) Date of Patent: Oct. 8, 2024

(54) DEODORANT COMPOSITIONS WITH METAL OXIDES

(71) Applicant: The Procter & Gamble Company, Cincinnati, OH (US)

(72) Inventors: David Arthur Sturgis, Montgomery, OH (US); Lindsey Michelle Britt, Deer Park, OH (US); Mahmoud Daffalla Eljack, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/409,946

(22) Filed: Aug. 24, 2021

(65) Prior Publication Data

US 2022/0054375 A1   Feb. 24, 2022

Related U.S. Application Data

(60) Provisional application No. 63/069,202, filed on Aug. 24, 2020.

(51) Int. Cl.

| | |
|---|---|
| *A61K 8/19* | (2006.01) |
| *A61K 8/34* | (2006.01) |
| *A61K 8/37* | (2006.01) |
| *A61K 8/891* | (2006.01) |
| *A61K 8/92* | (2006.01) |
| *A61Q 15/00* | (2006.01) |

(52) U.S. Cl.
CPC ............... *A61K 8/19* (2013.01); *A61K 8/342* (2013.01); *A61K 8/375* (2013.01); *A61K 8/891* (2013.01); *A61K 8/922* (2013.01); *A61Q 15/00* (2013.01); *A61K 2800/30* (2013.01); *A61K 2800/31* (2013.01); *A61K 2800/591* (2013.01)

(58) Field of Classification Search
None
See application file for complete search history.

(56) References Cited

U.S. PATENT DOCUMENTS

| | | |
|---|---|---|
| 5,723,110 A | 3/1998 | Yamamoto et al. |
| 5,744,130 A | 4/1998 | Guskey et al. |
| 8,673,327 B2 | 3/2014 | Lemoine et al. |
| 10,470,999 B2 | 11/2019 | Lesniak et al. |
| 10,555,884 B2 | 2/2020 | Sturgis et al. |
| 2010/0104612 A1 | 4/2010 | Cropper |
| 2012/0039833 A1 | 2/2012 | Brennan et al. |
| 2012/0045493 A1 | 2/2012 | Popoff et al. |
| 2016/0081895 A1 | 3/2016 | Elliott et al. |
| 2018/0168947 A1 | 6/2018 | Banowski et al. |
| 2018/0168985 A1 | 6/2018 | Banowski et al. |
| 2019/0105239 A1 | 4/2019 | Mikkelsen et al. |
| 2019/0105255 A1 | 4/2019 | Mikkelsen et al. |
| 2019/0336434 A1 | 11/2019 | Li |
| 2019/0350824 A1 | 11/2019 | Moujahed et al. |
| 2020/0016053 A1 | 1/2020 | Hilliard, Jr. et al. |
| 2022/0054366 A1 | 2/2022 | Sturgis et al. |
| 2024/0050327 A1 | 2/2024 | Sturgis |

FOREIGN PATENT DOCUMENTS

| | | |
|---|---|---|
| DE | 102008052747 A1 | 4/2010 |
| DE | 102018220966 A1 | 6/2020 |
| EP | 2189149 A1 | 5/2010 |
| WO | 2018122209 A1 | 7/2018 |
| WO | 2020000069 A1 | 1/2020 |

OTHER PUBLICATIONS

PCT Search Report and Written Opinion for PCT/US2021/047276 dated Dec. 23, 2021, 16 pages.
All Office Actions; U.S. Appl. No. 17/409,955, filed Aug. 24, 2021.
All Office Actions; U.S. Appl. No. 18/495,023, filed Oct. 26, 2023.

*Primary Examiner* — Patricia Duffy
*Assistant Examiner* — Garen Gotfredson
(74) *Attorney, Agent, or Firm* — Alexandra S. Anoff

(57) ABSTRACT

A deodorant composition comprising a metal oxide; a primary emollient; and at least one wax with a melting point above 50° C.: wherein the composition is anhydrous and aluminum-free; and wherein the composition has a pH greater than about 8.0 at 60 minutes as measured by the pH Release Test Method.

18 Claims, 1 Drawing Sheet

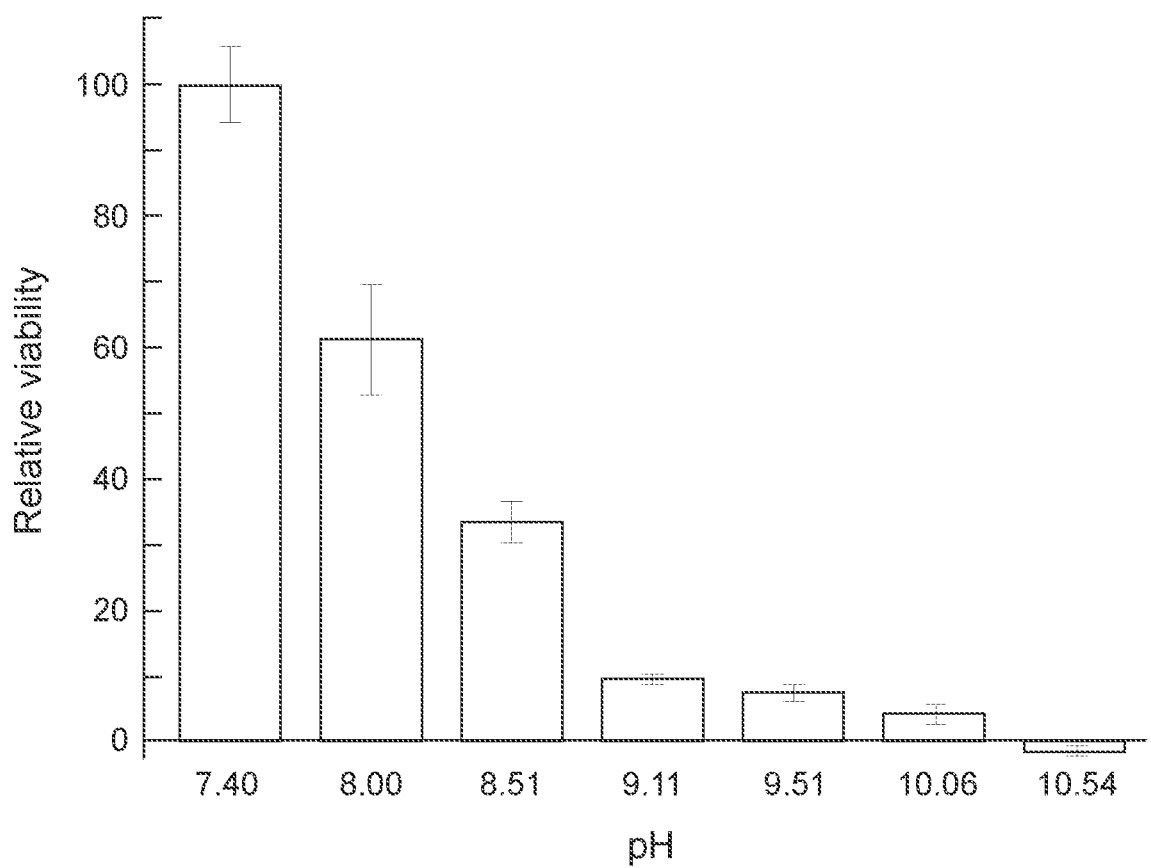

DEODORANT COMPOSITIONS WITH METAL OXIDES

FIELD OF THE INVENTION

The present disclosure relates to deodorant compositions and methods relating thereto.

BACKGROUND OF THE INVENTION

Many consumers are seeking more natural, aluminum-free deodorant offerings, in their preferred form of an anhydrous stick. Consumers also want these products to provide good odor protection through the release of a high pH which inhibits bacteria growth. Metal oxides like magnesium oxide are known to serve this function. However, what has been shown to be a challenge is having a formula chassis (primary emollient and wax system) with the water transport properties to efficiently release the metal oxide in sufficient quantities to achieve a pH sufficient to inhibit bacteria growth.

Thus, there remains a challenge to effectively formulate metal oxides into anhydrous aluminum-free sticks, in which the pH from the product comes close to achieving the pH of the metal oxide alone in water.

SUMMARY OF THE INVENTION

A deodorant composition comprising: a metal oxide; a primary emollient; and at least one wax with a melting point above 50° C.; wherein the composition is anhydrous and aluminum-free; and wherein the composition has a pH greater than about 8.0 at 60 minutes as measured by the pH Release Test Method.

BRIEF DESCRIPTION OF THE DRAWINGS

FIG. 1 is a graph showing the effect of pH on the viability of S. epidermidis.

DETAILED DESCRIPTION OF THE INVENTION

While the specification concludes with claims that particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

The components and/or steps, including those which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

The term "anhydrous" as used herein means substantially free of added or free water. From a formulation standpoint, this means that the anhydrous deodorant stick compositions of the present invention contain less than about 1%, and more specifically zero percent, by weight of free or added water, other than the water of hydration typically associated with the particulate deodorant active prior to formulation.

The term "ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

The term "majority" refers to greater than about 51% of the stated component or parameter.

"Substantially free of" refers to about 2% or less, about 1% or less, or about 0.1% or less of a stated ingredient. "Free of" refers to no detectable amount of the stated ingredient or thing.

The term "volatile" as used herein refers to those materials that have a measurable vapor pressure at 25° C. Such vapor pressures typically range from about 0.01 millimeters of Mercury (mm Hg) to about 6 mmHg, more typically from about 0.02 mmHg to about 1.5 mmHg; and have an average boiling point at one (1) atmosphere of pressure of less than about 250° C., more typically less than about 235° C. Conversely, the term "non-volatile" refers to those materials that are not "volatile" as defined herein.

Malodor Reduction

Many types of odor-causing bacteria become less viable at a higher pH. This is known by those of ordinary skill in the art and is shown, for example, by FIG. 1, a graph from the scientific literature, that shows how underarm odor-causing bacteria like, for example, Staphylococcus epidermidis, have decreased viability when the pH of the media goes above 8.0. FIG. 1 is taken from the Investigation of the Antibacterial Effect of Mesoporous Magnesium Carbonate, by Ken Welch, Mushtaq Ahmad Latifzada, Sara Frykstrand, and Maria Strømme, Division of Nanotechnology and Functional Materials, Department of Engineering Sciences, The Ångström Laboratory, Uppsala University, Box 534, 751 21

Uppsala, Sweden. The reference states, "To investigate the effect of pH on the viability of *S. epidermidis*, the pH of the MAA media was adjusted between 7.4 and 10.5 by the addition of NaOH, and the fluorescence was measured after 30 min." The FIGURE shows that the bacteria growth is reduced as the pH increases.

Certain high pH salts like magnesium oxide can achieve a pH greater than 10 in the presence of water. This pH is sufficient to significantly reduce the viability of odor-causing bacteria. However, it can be a challenge to formulate a consumer-acceptable cosmetic deodorant stick with these salts, such as magnesium oxide. The difficulty is to achieve a formulation that allows sufficient release of the pH powder to achieve a pH capable of impacting the viability of odor causing bacteria. That is, the bioavailability of the metal oxide powder must be sufficient to release the high pH when exposed to water from human sweat. This is because the choices of solvents and waxes used to formulate an acceptable stick can impede the release of the magnesium oxide powder from the product film, thus reducing the pH that can be achieved from the composition in a stick form.

Efficacy Enhancement

The primary function of many deodorants is to release a high pH powder that will inhibit the growth of odor-causing bacteria. The most consumer-preferred form of these deodorants is in a homogenous solid stick solidified by structurants. Structurants, like waxes, are used in this form to help give the stick its structure and stability. The downside of structurants is that they tend to interfere with the release of the high-pH powdered active from the composition and thus negatively impact the efficacy of the product. This issue is compounded as some consumers desire deodorant sticks made of natural or naturally-derived oils or other emollients that are non-volatile, which can further impede pH release.

While reductions in structurant level could be used to help increase active efficacy, this comes with its own challenges. Reducing the structurant level, for example, can negatively impact the stability of the product. As such, the desired solution is to find something that could be added to these types of solid products that would enhance water transport through the product film without negatively impacting stability of the product. Initial work focused on finding structurants and natural or naturally-derived oils that still enabled the release of high pH powders when combined with a wax to make a solid stick deodorant composition.

Further work focused on the addition of surfactants to the formulations to try and help break up the structurants and allow for better water transport. This enabled the use of some natural oils.

To illustrate the challenges of forming a homogenous and solid stick with sufficient bioavailability to achieve a pH greater than 8.0, in some cases greater than 8.5, in other cases greater than 9.0, or in still other cases a pH greater than 9.5, a 60-leg formulation design of experiments (DOX) was created. The DOX comprised a fixed amount of 10% magnesium oxide with 10 different emollients, each at 75% of the composition, and 6 different waxes each at 15% of the composition.

The samples were prepared by adding the wax and emollient in a beaker and heating to 85° C. until the wax was fully melted. Then the 10% magnesium oxide was added, and the batch was milled to break up any agglomerates and cooled to the pour temperature. The pour temperature was 70° C. for Ozokerite wax containing formulas, 60° C. for candelilla containing formulas, 65° C. for Castor Wax (hydrogenated castor oil) containing formulas, 60° C. for beeswax containing formulas (5 cst dimethicone and beeswax was poured at 65° C.), 60° C. for stearyl alcohol containing formulas, and 70° C. for behenyl behenate containing formulas.

Table 1 below shows list of emollients and waxes used in the DOX.

TABLE 1

| Antimicrobial pH Powder (10% of Composition) | Emollient (75% of the Composition) | Wax/Structurant (15% of the composition) |
|---|---|---|
| Magnesium Oxide | 5 cst Dimethicone<br>C12-15 Alkyl Benzoate<br>Isopropyl Myristate<br>Cyclopentasiloxane (D5)<br>Caprylic/Capric Triglyceride<br>Triheptanoin<br>Coconut Oil<br>Palm Kernal Oil<br>Sesame Seed Oil<br>Almond Oil | Stearyl Alcohol<br>Behenyl Behenate<br>Ozokerite<br>Castor Wax MP80 (hydrogenated Castor Oil)<br>Candelilla Wax<br>Beeswax |

The present inventors have discovered that not all combinations of metal oxides with emollients and waxes are sufficient to achieve a pH sufficient to significantly inhibit bacteria growth. Only a subset of emollient and wax combinations provide sufficient release of the metal oxide pH powders with exposure to water (sweat).

Surprisingly, Table 2 below shows only 19 of these 60 combinations from Table 1 were able to achieve a pH greater than 8.0 in the pH Release Method. The combinations of (5cst Dimethicone/Castor Wax) and (Cyclopentasiloxane (D5)/Castor Wax) were removed as they failed to form a homogenous composition due to the powders agglomerating and settling even under agitation.

Further, as shown in Table 2, as the pH release of the MgO was measured up to 1 hour in the pH Release Test Method described below, many combinations of solvents and waxes failed to achieve a sufficient pH, that is, a pH high enough, to inhibit bacteria growth with magnesium oxide. A minimum pH that allows magnesium oxide and other metal oxides to inhibit bacteria growth would be about 8.0. Many emollient and wax combinations do not provide sufficient solubility to the magnesium oxide to allow the magnesium oxide to raise the pH of the composition above 8.0. Alternatively, there are combinations in which the pH Release Test Method shows that the pH remains above 8.0 after 1 hour, which indicates that such combinations are able to deliver the magnesium oxide to a user of the deodorant stick.

TABLE 2

| | pH Release | | | | | | |
|---|---|---|---|---|---|---|---|
| Emollients and Waxes | Stearyl Alcohol | Behenyl Behenate | Ozokerite | Castor Wax | Candelilla | Beeswax | Average pH |
| 5 cSt Dimethicone | 10.2 | 9.4 | 9.2 | | 7.2 | 7.5 | 8.7 |
| C12-15 Alkyl Benzoate | 9.7 | 9.4 | 8.9 | 8.5 | 7.0 | 6.7 | 8.4 |

TABLE 2-continued pH Release

| Emollients and Waxes | Stearyl Alcohol | Behenyl Behenate | Ozokerite | Castor Wax | Candelilla | Beeswax | Average pH |
|---|---|---|---|---|---|---|---|
| Isopropyl Myristate | 10.3 | 9.0 | 7.5 | 8.5 | 7.4 | 6.8 | 8.3 |
| Cyclopenste siloxane (D5) | 9.5 | 9.3 | 8.9 | | 6.6 | 6.6 | 8.2 |
| Triheptanoin | 9.3 | 8.2 | 8.5 | 8.6 | 6.5 | 6.5 | 7.9 |
| Capric Caprylic Triglycerides | 9.0 | 8.9 | 7.5 | 7.2 | 6.5 | 6.8 | 7.6 |
| Coconut Oil | 6.8 | 6.8 | 7.5 | 6.8 | 6.8 | 6.7 | 6.9 |
| Palm kernel oil | 6.8 | 6.6 | 6.5 | 6.6 | 7.1 | 6.4 | 6.7 |
| Sesame Oil | 6.5 | 6.7 | 6.7 | 6.9 | 6.6 | 6.5 | 6.7 |
| Almond Oil | 6.8 | 6.6 | 6.5 | 6.9 | 6.3 | 6.3 | 6.5 |
| Average pH | 8.5 | 8.1 | 7.8 | 7.5 | 6.8 | 6.7 | 7.6 |

Additionally, Table 3 shows 18 of the combinations failed to form a solid stick as defined by a hardness penetration less than 200 mm*10 as measured by the Hardness Test Method. Table 4 includes the smaller subset of combinations that have sufficient hardness and that are able to form a homogenous, solid stick composition capable of delivering a pH greater than 8.0 in the pH release method.

Surprisingly, this shows it remains a challenge to combine emollients and waxes sufficiently to both make a homogenous, solid stick deodorant with a pH greater than 8.0 in the pH Release Method to enable sufficient malodor performance.

TABLE 3

| Emollients and Waxes | Stearyl Alcohol | Sehenyl Sehenate | Ozokerite | Castor Wax | Candelilla | Beeswax |
|---|---|---|---|---|---|---|
| 5 cSt Dimethicone | <200 | <200 | <200 | >250 | <200 | <200 |
| C12-15 Alkyl Benzoate | >250 | <200 | <200 | >250 | <200 | >250 |
| Isopropyl Myristate | >250 | <200 | <200 | 230 | 230 | >250 |
| Cyclopenta siloxane (D5) | <200 | <200 | <200 | >250 | <200 | >250 |
| Triheptanoin | >250 | <200 | <200 | >250 | <200 | >250 |
| Capric Caprylic Triglycerides | >250 | <200 | <200 | >250 | <200 | >250 |
| Coconut Oil | <200 | <200 | <200 | <200 | <200 | <200 |
| Palm kernel oil | <200 | <200 | <200 | <200 | <200 | <200 |
| Sesame Oil | >250 | <200 | <200 | <200 | <200 | >250 |
| Almond Oil | >250 | <200 | <200 | >250 | <200 | <200 |

TABLE 4

| Emollients and Waxes | Stearyl Alcohol | Behenyl Behenate | Ozokerite | Castor Wax | Candelilla | Beeswax |
|---|---|---|---|---|---|---|
| 5 cSt Dimethicone | 10.2 | 9.4 | 9.1 | | 7.2 | 7.5 |
| C12-15 Alkyl Benzoate | | 9.4 | 8.9 | | 7.0 | |
| Isopropyl Myristate | | 9.0 | 7.5 | | | |
| Cyclopenta siloxane (DS) | 9.5 | 9.3 | 8.9 | | 6.6 | |
| Triheptanoin | | 8.2 | 8.5 | | 6.5 | |
| Capric Caprylic Triglycerides | | 8.9 | 7.5 | | 6.5 | |
| Coconut Oil | 6.8 | 6.8 | 7.5 | 6.8 | 6.8 | 6.7 |
| Palm kernel oil | 6.8 | 6.6 | 6.5 | 6.6 | 7.1 | 6.4 |
| Sesame Oil | 6.5 | 6.7 | 6.7 | 6.9 | 6.6 | |
| Almond Oil | | 6.6 | 6.5 | | 6.3 | 6.3 |

From Table 5, even Comparative Example #1, which is a marketed product comprising magnesium oxide, but without the inventive emollient and wax structure described herein, was not able to achieve a pH above 8.0 under the pH Release Test Method, meaning it could not deliver the magnesium oxide and its antimicrobial benefit. Surprisingly, Comparative Example #1's combination of almond oil and beeswax was the lowest pH result in the DOX, which suggests a significant decrease in bioavailability of the magnesium oxide when used in this emollient and wax combination.

TABLE 5

| Comparative Example #1 | Comparative Example #2 |
|---|---|
| Magsol Sweet Orange scented deodorant: marketed with Ingredient statement: Sweet Almond Oil, | US 2019/0350824 example #3 Ingredients: Hydrogenated polydecene 16% Isopropyl myristate 15% |

TABLE 5-continued

| Comparative Example #1 | Comparative Example #2 |
|---|---|
| Beeswax, Magnesium Oxide, Sweet Orange Oil | Magnesium Oxide 15% Polydimethylsiloxane 14% Synthetic Wax Cirebelle 108 12% |

TABLE 5-continued

| Comparative Example #1 | Comparative Example #2 |
|---|---|
|  | PPG-14 Butyl ether 10% |
|  | Coconut Oil 10% |
|  | Synthetic Wax Cirebelle 303 5% |
|  | Peg-8 Distearate 2.5% |
|  | Fragrance 0.5% |
| pH-6.0 | pH-7.8 |

Comparative Example #2, from US 2019/0350824 example #3, teaches use of magnesium oxide in a solid stick composition, but without the inventive emollient and wax structure described herein. The example #3 was not able to achieve a pH above 8.0 under the pH Release Test Method, meaning it could not deliver the magnesium oxide and its enhanced antimicrobial benefit. That is true even though that example used 15% magnesium oxide vs the 10% used in the DOX. Additionally, higher levels can have consumer negative tradeoffs, such as residue and draggy feel. Therefore, surprisingly and beyond expectations, a more efficient emollient/wax combination is more critical to delivering enhanced antimicrobial pH than even the level of antimicrobial powder.

Comparative example #2 also shows the importance of combinatory effects of multiple emollients and waxes, suggesting the importance of the pH Release method to assess overall bioavailability. In the DOX above from Table 2, there are combinations using isopropyl myristate that resulted in a pH above 8.0. However, there were no combinations in Table 2 using coconut oil that resulted in a pH greater than 8.0. So, in comparative example #2, it is likely that the inclusion of coconut oil, and likely other ingredients, reduces the overall bioavailability of the magnesium oxide.

Two emollients in the 60-leg DOX showed promise, as compositions comprising either caprylic/capric triglyceride or cylcopentasiloxane, when combined with behenyl behenate, showed a pH above 8.9 under the pH Release Test Method. But when the caprylic/capric triglyceride was paired with candelilla wax, the pH at 60 minutes was only 6.5 and was insufficient. Likewise, when cyclopentasiloxane was paired with candelilla the pH was only 6.6. However additionally, when the caprylic/capric triglyceride or cyclopentasiloxane was combined with a fatty alcohol like stearyl alcohol, they were also able to achieve a sufficient pH. This shows again that the emollient/wax combination is critical to the release of the pH powder.

However, some emollient/wax combinations were more likely to result in a pH greater than 8.0 than others as shown by the averages in Table 2. Silicones like 5 cst dimethicone, and cyclopentasiloxane; along with triglycerides like caprylic/capric triglyceride and triheptanoin showed the most promise. Especially when combined with ester waxes like behenyle behenate, or ozokerite, or a fatty alcohol like stearyl alcohol.

As shown in Table 6, certain combinations of emollients and wax form a structurant in which magnesium oxide is able to be delivered. Table 6 shows emollient/wax combinations in which the pH Release Test Method indicated a pH of at least 8.0.

A table of inventive combinations: (From Table 2 pH>8.0)

TABLE 6

| Wax | Emollient(s) |
|---|---|
| Stearyl Alcohol | Cyclopentasiloxane |
|  | 5 cst Dimethicone |
| Behenyl Behenate | 5 cst Dimethicone |
|  | C12-15 Alkyl Benzoate |
|  | Isopropyl Myristate |
|  | Cyclopentasiloxane |
|  | Triheptanoin |
|  | Caprylic/Capric Triglyceride |
| Ozokerite | 5 cst Dimethicone |
|  | C12-15 Alkyl Benzoate |
|  | Isopropyl Myristate |
|  | Cyclopentasiloxane |
|  | Triheptanoin |
|  | Caprylic/Capric Triglyceride |
|  | Coconut Oil |
| Castor Wax | C12-15 Alkyl Benzoate |
|  | Isopropyl Myristate |
|  | Triheptanoin |

Table 7 below, shows examples of Comparative formulas that do not meet the 8.0 pH release.

TABLE 7

|  | Comparative 3 | Comparative 4 | Comparative 5 | Comparative 6 | Comparative 7 | Comparative 8 |
|---|---|---|---|---|---|---|
| Magnesium Oxide | 10 | 10 | 10 | 10 | 10 | 10 |
| Capric/Caprylic Triglyceride |  |  |  | 75 |  |  |
| Coconut Oil |  |  | 75 |  |  |  |
| Palm kernel oil |  |  |  |  | 75 |  |
| Sesame Oil |  |  |  |  |  | 75 |
| Almond Oil | 75 | 75 |  |  |  |  |
| Ozokerite |  | 15 | 15 |  | 15 | 15 |
| Candelilla |  |  |  | 3.5 |  |  |
| Beeswax | 15 |  |  |  |  |  |
| pH Release Method @ 60 mins | 6.3 | 6.5 | 7.5 | 6.5 | 6.5 | 6.7 |

Table 8 includes additional inventive full formulas that do exceed a pH of 8.0 after 60 minutes in the pH Release method.

TABLE 8

|  | Inventive #1 | Inventive #2 | Inventive #3 |
|---|---|---|---|
| Cyclopentasiloxane | 46.85 |  |  |
| Caprylic/Capric Triglyceride |  |  | 53 |
| Triheptanoin |  | 51.25 |  |
| Stearyl Alcohol | 18.5 |  |  |
| Castor Wax | 5 |  |  |
| Behenyl Behenate |  |  |  |
| Rice Bran Wax | 0.2 |  |  |
| Ozokerite |  | 9.5 | 9.5 |
| Magnesium Oxide | 8 | 8 | 8 |
| Sodium Bicarbonate |  | 2 | 2 |
| Tapioca Starch |  |  | 20 |

TABLE 8-continued

|  | Inventive #1 | Inventive #2 | Inventive #3 |
|---|---|---|---|
| Nordic Barley Powder |  | 22 |  |
| Mineral oil | 8 |  |  |
| PPG-14 butyl ether | 8 |  |  |
| Cyclodextrin | 2 | 4 | 4 |
| Silica | 0.5 |  |  |
| Petrolatum | 0.5 |  |  |
| Piroctone Olamine | 0.4 |  |  |
| Behenyl Alcohol | 0.05 |  |  |
| Coconut Oil |  | 1 | 1 |
| Shea Butter |  | 0.5 | 0.5 |
| Fragrance | 2 | 1.75 | 2 |
| pH Release @ 60 mins | 8.9 | 8.0 | 8.1 |

Consumers seeking aluminum-free, naturally derived deodorants are also seeking products that are free from controversial ingredients, due to publicity around the ingredients' safety, farming, or labor practices. Therefore, in some embodiments, it may be ideal to have the deodorant free from solvents or emollients such as, for example, isopropyl palmitate, ppg-14 butyl ether, coconut oil, almond oil, palm kernel oil, propanediol, propylene glycol, and/or silicones.

In some embodiments, it may be ideal to have the deodorant free from certain waxes, such as, for example, beeswax, stearyl alcohol, behenyl alcohol, candelilla wax, and/or carnauba wax. In some embodiments, it may be ideal to have the deodorant free from powders such as calcium hydroxide, sodium bicarbonate, magnesium hydroxide, arrowroot powder, zinc oxide, and/or corn starch. In some embodiments, it may be ideal to have the deodorant free from all fatty acid ester oils like isopropyl myristate. In some embodiments, it may be ideal to have the deodorant free from palm derived materials. In some embodiments, it may be ideal to have the deodorant free from triheptanoin.

A. Structurants

The deodorant compositions of the present invention may comprise a suitable concentration of structurants to help provide the compositions with the desired viscosity, rheology, texture and/or product hardness, or to otherwise help suspend any dispersed solids or liquids within the composition.

The primary structurant in the present invention may have a melting point of at least about 50° C., in some embodiments from about 50° C. to about 70° C., and in other embodiments from about 50° C. to about 75° C., and in other embodiments from about 60° C. to about 80° C. A primary structurant is defined as the structurant that is present in the composition in the greatest amount (liquid triglycerides are not considered a structurant in this context). Some embodiments may have just a single structurant, so may have only a primary structurant. Other embodiments may have a primary structurant and then secondary structurants, those structurants that are used in a lesser amount than the primary structurant. The primary structurant may be a wax selected from the group consisting of ozokerite, paraffin, polyethylene-based waxes, and combinations thereof. The primary structurant may be an ester-based wax selected from the group consisting of behenyl behenate, stearyl behenate, stearyl stearate, stearyl palmitate, and combinations thereof. The primary structurant may be, for example, ozokerite, behenyl behenate, fatty alcohols, or combinations thereof.

The primary structurant may comprise from about 5% to about 20%, in some cases from about 7% to about 17%, by weight of the deodorant stick. The secondary structurants may cumulatively comprise about 12% or less, or about 8% or less by weight of the deodorant stick, in some embodiments less than about 5%, less than about 3%, or less than about 1% by weight of the deodorant stick. In some embodiments, the deodorant stick may be free of or substantially free of any secondary structurants.

B. Emollients

Emollients are often used as the largest percentage of the composition. They provide the solvency for the structurants and improve the feel of the stick during application versus sticks made of structurants alone.

As discussed, an effective and consumer-preferred emollient may be a liquid triglyceride. Derived directly from plant sources, they are often short chains. Longer chain triglycerides may be used as structurants in deodorant or antiperspirant sticks, but the triglycerides of the present invention are liquid at room temperature (25° C.) and tend to be shorter chains. An example may be caprylic/capric triglyceride (coconut oil fractionated). They can be made with a mixture of C7-C10 triglycerides. In some embodiments this could be all C7's like triheptanoin. And in others this could be a mixture of C8/C10 like Caprylic/Capric Triglyceride. Or a mixture thereof of any in this paragraph.

The present inventive deodorant sticks may comprise at least about 20% by weight of one or more liquid triglyceride, in some embodiments, at least about 25%, at least about 30%, at least about 35%, at least about 40%, at least about 45%, or at least about 50% liquid triglyceride, by weight of the composition. In some embodiments, the deodorant stick comprises from about 25% to about 60%, by weight of the composition, of one or more liquid triglyceride, from about 25% to about 50%, from about 30% to about 50%, from about 35% to about 60%, from about 35% to about 50%, from about 40% to about 60%, or from about 40% to about 50%, by weight of the composition, of one or more liquid triglyceride. In general, the greater amount of liquid in the formulation, the softer the deodorant stick may be. The more solids in the formulation leads to greater hardness. Because achieving a sufficient softness in a deodorant stick with natural ingredients can be a challenge, it can be beneficial to formulate with higher amounts of liquids such as liquid triglyceride. The level of liquid triglyceride as referred to herein may be the sum total of one or more types of liquid triglyceride in a particular deodorant stick.

In some embodiments, additional emollients may be used, such as plant oils (generally used at less than 10% by weight) including olive oil, coconut oil, sunflower seed oil, jojoba seed oil, avocado oil, canola oil, and corn oil. Additional emollients including mineral oil; shea butter, PPG-14 butyl ether; isopropyl myristate; petrolatum; butyl stearate; cetyl octanoate; butyl myristate; myristyl myristate; C12-15 alkylbenzoate (e.g., Finsolv.™.); octyldodecanol; isostearyl isostearate; octododecyl benzoate; isostearyl lactate; isostearyl palmitate; isobutyl stearate; dimethicone, and any mixtures thereof. In some embodiments a silicone may be used like dimethicone or cyclopentasiloxane. As discussed, these emollients could also be combined with a surfactant to ensure water transport and water solubility sufficient to inhibit bacteria growth. And in some embodiments the silicone would be combined with both a surfactant and an additional emollient with sufficient water transport like a liquid triglyceride.

Emollient/Wax Combinations

What the present inventors have discovered is that when formulating an anhydrous deodorant stick with metal oxides, the combination of the emollient and wax is critical to allowing the release of the metal oxides from the composition and to achieving the desired pH that provides a strong antimicrobial effect.

Examples of combinations that allow for the release of the metal oxides include, but are not limited to: a liquid triglyceride emollient with a wax selected from the group consisting of ozokerite, paraffin, polyethylene-based waxes, and combinations thereof; a liquid triglyceride emollient with ester-based waxes selected from the group consisting of behenyl behenate, stearyl behenate, stearyl stearate, stearyl palmitate, and combinations thereof; a silicone emollient with a wax selected from the group consisting of ozokerite, paraffin, polyethylene-based waxes, and combinations thereof; a silicone emollient with a an ester-based wax selected from the group consisting of behenyl behenate, stearyl behenate, stearyl stearate, stearyl palmitate, and combinations thereof. Other possible combinations may include an emollient such as a liquid triglyceride or silicone combined with a fatty alcohol.

C. Metal Oxides

The present inventions may include metal oxides, including, for example, magnesium oxide, zinc oxide, and/or calcium oxide. The metal oxide may be utilized in levels from about 0.1% to about 30%, alternatively from about 2% to about 20%, alternatively from about 5% to about 15%, or alternatively from about 8% to about 13%, by weight of the composition.

D. Additional Antimicrobials

The present invention may include one or more antimicrobial compositions. For example, antimicrobials may include, without being limited to, baking soda, hexamidine, magnesium carbonate, zinc carbonate, thymol, magnesium hydroxide, magnesium hydroxide and magnesium carbonate hydroxide (dead sea salt), partially carbonated magnesium hydroxide, sodium carbonate, calcium carbonate, magnesium carbonate hydroxide, cinnamon essential oil, cinnamon bark essential oil, cinnamic aldehyde, polyvinyl formate, salycilic acid, niacinamide, phenoxyethanol, eugenol, linolenic acid, dimethyl succinate, citral, triethyl citrate, sepiwhite, an substituted or unsubstituted 2-pyridinol-N-oxide material (piroctone olamine), and combinations thereof. The deodorant stick may be free of or substantially free of a substituted or unsubstituted 2-pyridinol-N-oxide material.

In general, the total amount of antimicrobial used in the present invention may be from about 0.1% to about 30%, by weight, of the deodorant. Some antimicrobials may be used in amounts as low as about 0.1%, by weight of the deodorant stick, such as if using piroctone olamine or hexamidine as the primary antimicrobial, while others could be as high as about 25% if using magnesium hydroxide or magnesium hydroxide and magnesium carbonate hydroxide as the primary antimicrobial (primary antimicrobial being the antimicrobial present in the composition in the highest amount). In the latter cases, baking soda might still be used at a lower level, such as from about 0.1% to about 6%, as a secondary antimicrobial, or not at all.

Any of the antimicrobials of the present invention may be used as powders. It is believed that antimicrobial powders may provide a better deposition and have more longevity on the skin than antimicrobials delivered in a different form. In addition, it is believed that antimicrobial powders of a certain average particle size, typically from about 1 micron to about 5 microns, may provide a significant increase in antimicrobial efficacy.

Many antimicrobials can be effective at minimizing the skin surface bacteria. However, as a leave-on product where odor may not occur until later, even hours after application, deodorant antimicrobials are needed that will be effective for long periods of time. So while deodorant antimicrobials may be effective immediately upon application on the skin, it is believed that odor comes back quickly because the bacteria living around the hair follicle can quickly repopulate the skin surface bacteria. Historical approaches using high skin penetrating liquid antimicrobials to affect this region (for example, hexanediol) can cause irritation. Therefore, the present invention may target methods and mechanisms that can more effectively deliver antimicrobials not only to the skin surface, but to the bacteria in and around the hair follicle. While not wanting to be bound to the theory, the inventors of the present inventor believe that powders, specifically powders with an average particle size of less than about 10 microns, in some cases from about 1 micron to about 5 microns, are more efficient at getting into the hair follicle where the bacteria live and repopulate the skin surface. In some embodiments, the antimicrobials may be a combination of larger sized particles and smaller particles that are from 1 to 10 microns. As noted above, solids such as powders can impact the overall hardness of the deodorant stick. In general, greater amounts of powders and structurants increase the deodorant stick's hardness.

The present inventors have discovered that the water solubilities of certain components in the solid stick deodorant have great importance. Some deodorant ingredients will bring in moisture to the batch, which can solvate these components to different extents when the water evaporates and subsequently recondenses as free water in the batch. Certain batch processing conditions (such as a closed top on the tank) could more effectively trap this water in the tank, where it is then free to interact with components of the batch. For example, highly water soluble alkaline powders can contribute negatively towards natural and essential oil stability when dissolved. This is because many natural and essential oils contain a broad range of perfume chemicals, many of which can undergo degradation reactions when exposed to extreme pH or heat. This is why many natural and essential oils have shorter shelf lives than many commercial synthetic chemicals or perfumes. And certain antimicrobials may cause irritation due to high water solubility. Further, high water solubility can lead to grittier products as the more water soluble powders can agglomerate when exposed to moisture released from powders during the heat of manufacture.

Thus, embodiments of the present invention may include an antimicrobial with a low water solubility. An antimicrobial with a low water solubility may be, in some embodiments, an antimicrobial with a water solubility of at most 90 g/L at 25° C., in other embodiments at most 75 g/L at 25° C., or in still other embodiments at most 50 g/L at 25° C.

Materials with a water solubility above 90 g/L @25° C. include but are not limited to: potassium carbonate, potassium bicarbonate, sodium carbonate, sodium sesquicarbonate, triethyl citrate, and baking soda. Materials with a water solubility below 90 g/L @25° C. include but are not limited to: beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salycilic acid, phenoxyethanol, eugenol, linolenic acid, dimethyl succinate, citral, and triethyl citrate. Each of beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salycilic acid, phenoxyethanol, eugenol, linolenic acid, dimethyl succinate, and citral have a water solubility below 75 g/L @25° C., below 50 g/L @25° C., below 1 g/L @25° C., and below 0.2 g/L @25° C.

E. Perfume

Perfumes are often a combination of many raw materials, known as perfume raw materials. Any perfume suitable for use in a deodorant composition may be used herein. In some embodiments, the deodorant composition may be free of, or substantially free of a synthetic fragrance. A synthetic fragrance is one mostly derived through chemical synthesis where the starting material is no longer intact, but is converted to the new fragrance chemical.

A natural or essential oil fragrance is a result of natural sources wherein the fragrance material is not altered (chemically modified) but extracted from its natural source. These sources can include, but are not limited to, bark, flowers, blossoms, fruits, leaves, resins, roots, bulbs, and seeds. Natural or essential oils go through an extraction process instead of chemical synthesis. Extraction processes include, but are not limited to, maceration, solvent extraction, distillation, expression of a fruit peel, or effleurage.

Additional Chassis Ingredients

Starch

The deodorant composition may comprise a starch powder for dry feel or wetness absorption. Examples include but are not limited to arrowroot powder, tapioca starch, Nordic barley powder, and corn starch.

Solvent

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv.™.), octyldodecanol, isostearyl isostearate, octododecyl benzoate, isostearyl lactate, isostearyl palmitate, and isobutyl stearate.

Other Optional Ingredients

The anhydrous deodorant compositions of the present invention may further comprise any optional material that is known for use in antiperspirant and deodorant compositions or other personal care products, or which is otherwise suitable for topical application to human skin.

One example of an optional ingredient is a scent expression material. Scent expression or release technology may be employed with some or all of the fragrance materials to define a desired scent expression prior to use and during use of the deodorant products. Such scent expression or release technology can include cyclodextrin complexing material, like beta cyclodextrin. Other materials, such as, for example, starch-based matrices or microcapsules may be employed to "hold" fragrance materials prior to exposure to bodily-secretions (e.g., perspiration). The encapsulating material may have release mechanisms other than via a solvent; for example, the encapsulating material may be frangible, and as such, rupture or fracture with applied shear and/or normal forces encountered during application and while wearing. A microcapsule may be made from many materials, one example is polyacrylates.

Another example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, chelants, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Method of Making

The deodorant stick products of the present invention may be made by mixing all the components of the products in an open-top or vented tank. Many powders come with bound moisture, especially naturally high moisture powders like starches. In a mostly anhydrous process with waxes, melting the waxes above their melt point can release this bound water as the batch temperature increases. In a closed tank process this water vapor will condense in the tank and drip back into the batch as water. This water can interact with the most water soluble ingredients in the batch to have negative effects on the product, including releasing the pH of any antimicrobial ingredient, which can then degrade any perfume ingredients in the batch. Additionally, the condensed water can interfere with the wax and produce a stick softer than intended.

The present invention reduces the risk of these negative consequences. The ideal process remedy for this behavior is to produce the batches in one of four ways:
1. An open tank system where the water vapor can leave the batch tank to reduce or eliminate condensation.
2. A vented closed tank to also remove water vapor during the batch process.
3. A dual phase process where the moisture containing powders can be put into the cold phase separate from the wax phase which is heated. These two phases are then mixed before filling.
4. A low residence time batch process for a closed system, where the product has less than 3 hours residence time above 50° C. to reduce the rate of reaction from the moisture.

A method of making a deodorant composition or stick may comprise the steps of combining any of the herein described deodorant composition components in an open tank system or a vented closed tank. The components may be mixed, heated, and then cooled into a stick product. In some embodiments, the deodorant components may comprise at least about 40% of a liquid triglyceride, by weight of the composition, and an antimicrobial in an open tank system, heating the components, mixing the components, and cooling the components.

Test Methods
pH Release Method

The pH Release Method measures pH as a function of time under in vitro conditions that are chosen to approximately mimic the condition of the laid product in the axilla interacting with the emerging sweat and the transdermal water loss. The pH is recorded over a period of 60 minutes with one-second time resolution, and the pH at 60 minutes. All experiments are done in laboratory conditions of 23±2° C. and 50±5% relative humidity environment unless otherwise specified.

Materials and Apparatus

An artificial eccrine sweat solution is prepared by dissolving 0.2 g bovine serum albumin, or BSA, (biotechnology grade, Cat. No. 9048-46-8, VWR International, Radnor, Pennsylvania, USA, or equivalent) in 1000 mL deionized water (resistivity of 18.2 MΩ·cm). This solution can be stored for up to 1 week at 5° C. It is equilibrated to lab temperature (ensuring that any solids precipitated in cool storage redissolve) before use.

An analytical four-place balance with precision of 0.0001 g is used to determine mass. An autotitrator with pH probe (such as T70 Titration System w/Rondo 20-Place Sampler and DGi115-SC, Mettler-Toledo, Toledo, Ohio, USA, or equivalent) is used to enable pH measurement with one-second resolution. The pH probe is calibrated with buffers of pH 4.0, 7.0, and 10.0 prior the measurement, and the buffer is stirred for 2 minutes before the measurement and during the measurement and while at least two minutes before accepting the pH calibration point.

Sample Preparation

In the case that finished, packaged deodorant is sampled, each specimen analyzed is collected from the top 0.8 cm of a freshly opened package using a 6-mm-diameter transfer tube (such as 190195P Spectrum Laboratories Inc., Irving. Texas, USA, or equivalent). Otherwise, composition is sampled with the same style transfer tube from a freshly opened vessel in which the composition has been allowed to equilibrate to lab temperature. In either case, a 1.00±0.05 g of sample composition in the transfer tube is pushed to uniformly coat the bottommost portion of titration cup (such as 51109389 Mettler Toledo, Toledo, Ohio, USA, or equivalent)

Timed pH-Curve Determination

Release of pH-adjusting actives is assessed by monitoring the pH of the eccrine sweat solution using the automated pH logging functionality of an autotitrator. Briefly, the 1.00±0.05 g of product is added to a100 mL titration sample beaker (such as part 51109388, Mettler Toledo, Ohio, USA, or equivalent). 40 mL of the artificial sweat is delivered within about 5 seconds to the product in beaker, and the pH of the solution is thenceforth continuously recorded for one hour at one-second intervals without stirring. The pH at any given time point can be recorded and reported as pH as a given time over the one-hour period. For example, the pH recorded at 3600 seconds (60 minutes) is recorded and reported to the nearest tenth as pH at 60 minutes.

Water Vapor Sorption Test Method

The Water Vapor Sorption Test Method is used to determine the amount of water vapor sorption that occurs in a raw material or composition between being conditioned with a first environmental state and a second environmental state at elevated temperature and humidity. In this method, product is spread thinly on an inert substrate, and the mass change associated with being conditioned with differing environmental states is captured in a dynamic vapor sorption instrument. The resulting mass gain, expressed as a mass gain per 100 g of composition or raw material, is reported.

This method makes use of a SPSx Vapor Sorption Analyzer with 1 μg resolution (ProUmid GmbH & Co. KG, Ulm, Germany), or equivalent dynamic vapor sorption (DVS) instrument capable of controlling percent relative humidity (% RH) to within ±3%, temperature to within ±2° C., and measuring mass to a precision of ±0.01 mg. The laboratory environment is maintained at 22±2° C. and 40±20% RH, and all samples and materials are equilibrated to the laboratory conditions for at least 24 hours prior to performing this method. Formulations that have been fully packed are equilibrated in their unused, unopened state. Raw materials or experimental formulations that may not have been fully packed are equilibrated to the laboratory environment in a sealed glass jar with a headspace volume representing no greater than 25% of the overall jar volume.

Samples are prepared in the laboratory environment described above. A 20.0±2.0 mg specimen of raw material or composition is spread evenly on a circular (18 mm diameter) disc made of polytetrafluoroethane (PTFE) 50±5 μm (0.002 inches) in thickness. (The disc of PTFE is tared beforehand along with an aluminum sample pan appropriate for the DVS instrument. In this method, all mass measurements presume the subtraction of the mass of the PTFE and sample pan).

The PTFE disc on which raw material or composition specimen has been spread is placed in the DVS instrument with the DVS instrument set to 22° C. and 30% RH at which point an initial mass of the specimen is immediately recorded to a precision of 0.01 mg or better. This is defined as $m_1$. After the specimen is in the DVS for a duration of 48 hours at this environmental setting, the mass $m_2$ of the specimen is recorded to a precision of 0.01 mg or better. The DVS is then set to 32° C. and 70% RH, and the specimen remains in the DVS for a duration of 200 hours at this environmental setting with mass being measured and recorded every 15 minutes to a precision of 0.01 mg or better. The maximum mass measured during this 200-hour hold is defined as mass $m_3$.

For a particular specimen, the Water Vapor Sorption Per 100 Grams is defined as $$\text{Water Vapor Sorption Per 100 Grams} = \frac{m_3 - m_2}{m_1} \times 100 \text{ g}$$

The Water Vapor Sorption Per 100 Grams is reported in units of grams to the nearest 0.1 g. with units of g Abs/100 g.

In some embodiments of the present invention, the composition may have a dynamic vapor sorption greater than 1.00 g Abs/100 g. Some composition combinations that have a high pH release may also have a high vapor absorption per gram of product. The DVS data may show the reverse side of the pH Release data, in that the pH Release shows that in water the metal oxide powder can leave the film structure of the stick and raise the pH of the water or sweat, while the DVS can show that the film can attract more water into it, suggesting there would then be more pH release as well with greater or faster contact of water and the film.

Hardness Test Method—Penetration Measurement for Deodorant Finished Products

The penetration test is a physical test method that provides a measure of the firmness of waxy solids and extremely thick creams and pastes with penetration values not greater than 250 when using a needle for D1321. The method is based on the American Society for Testing and Materials Methods D-5, D1321 and D217 and DIN 51 579 and is suitable for all solid antiperspirant and deodorant products.

A needle or polished cone of precisely specified dimensions and weight is mounted on the bottom of a vertical rod in the test apparatus. The sample is prepared as specified in the method and positioned under the rod. The apparatus is adjusted so that the point of the needle or cone is just touching the top surface of the sample. Consistent positioning of the rod is critical to the measured penetration value. The rod is then released and allowed to travel downward, driven only by the weight of the needle (or cone) and the rod. Penetration is the tenths of a millimeter travelled following release.

| APPARATUS | SUGGESTED TYPE (OR EQUIVALENT) |
| --- | --- |
| Penetrometer with Timer | Penetrometer Suitable For ASTM D-5 and D-1321 methods; Examples: Precision or Humboldt Universal Penetrometer (Humboldt Manufacturing, Schiller Park, IL USA) or Penetrometer Model PNR10 or PNR12 (Petrolab USA or PetroTest GmbH). |
| Penetration Needles | Antiperspirant or deodorant solids can use: Needles as specified for ASTM Method D-5, NIST Certified, Fisher Scientific #01-512. Needles as specified for ASTM Method D 1321/DIN 51 579, Officially certified, Taper-Tipped needle, No. H-1310, Humboldt Mfg. |

General Instructions—All Penetrometers—Keep the instrument and needles/probes clean at all times, free from dust and grime. When not in use, store needles in a suitable container to avoid damage.
Periodic calibration should confirm:
 Electronic Timer is correctly set. Verify against an independent stopwatch if unsure.
 Shaft falls without visible signs of frictional resistance.
 Ensure the total weight of the shaft and needle is 50±0.2 grams when the shaft is in free fall.
Note: for modern, automated or digital systems this may be performed automatically and confirmed through annual calibration.
At time of use confirm:
 Electronic Timer is correctly set to 5.0 seconds.
 The appropriate needle is installed and is clean, straight and without obvious defects (visual inspection)
 The penetrometer is level and the shaft is clean, straight and falls freely (visual inspection)
 Once level, avoid shifting the position of the unit to maintain level.
Sample Preparation and Measurement
 1. On a deodorant stick that has cooled ambiently to a temperature between 22° C. and 26° C. for at least 24 hours, slice off top ½ inch of product to achieve a flat surface with a wire cutter drawn across the upper lip of the canister. This will be the reading for the Top of the stick.
 2. For the first sample to be tested, lubricate the ASTM D-5 needle by gently wiping with a lint-free tissue coated with a small amount of the product to be tested. This small amount is typically taken from the shaved top.
 3. Place the canister in the appropriate location for the measurement. Locate the sample so the needle will penetrate the product 9-11 mm from the inside of the canister wall on the long axis.
 4. Using the coarse and fine adjustments, align the height of the penetrometer mechanism head so that the point of the penetrating needle is just touching the surface of the sample.
 A weak light at the side of the penetrometer which casts a shadow of the needle on the surface of the sample may be helpful in determining this contact. When a light area on the sample cannot be seen at the end of the tip of the needle's shadow, the needle height over the sample is correctly adjusted. The light should not be strong enough to heat or melt the sample surface. The needle should be just close enough to scratch the sample surface.
 5. Perform the penetration measurement at this location by releasing the needle. Record the result.
 6. Repeat Steps 2 through 4 at the other test point, i.e., at the other point 9-11 mm inside of the canister wall on the long axis.
To report results, units for penetration are tenths of a millimeter (⅒ mm=100 microns). For example, a result of 80 units is 80 mm*10 or 8 mm. Report the average results of at least 4 total measurements from 2 different sticks, report to the nearest tenth of a millimeter.
 7. For the Bottom of the stick measurements, turn the canister up until only 1-2" of product is left on the elevator, slice the product to achieve a flat surface with a wire cutter drawn across the upper lip of the canister. Then repeat Steps 2-6 to measure and record the Bottom of the stick harness.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". All numeric values (e.g., dimensions, flow rates, pressures, concentrations, etc.) recited herein may be modified by the term "about", even if not expressly so stated with the numeric value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A homogeneous deodorant stick composition comprising:
   a. a metal oxide;
   b. a primary emollient; and
   c. at least one wax with a melting point above 50° C.;
   wherein the composition is anhydrous and aluminum-free;
   wherein the composition is free of calcium hydroxide;
   wherein the composition has a pH greater than about 8.0 at 60 minutes as measured by the pH Release Test Method; and
   wherein the composition has a hardness penetration less than 200 mm*10 as measured by the Hardness Test Method.

2. The composition of claim 1, wherein the metal oxide is chosen from magnesium oxide, calcium oxide, or mixtures thereof.

3. The composition of claim 1, further comprising an additional antimicrobial chosen from piroctone olamine, beryllium carbonate, magnesium carbonate, calcium carbonate, magnesium hydroxide, magnesium hydroxide and magnesium carbonate hydroxide, partially carbonated magnesium hydroxide, piroctone olamine potassium carbonate, potassium bicarbonate, sodium carbonate, sodium sesquicarbonate, sodium bicarbonate, hexamidine, zinc carbonate, thymol, polyvinyl formate, salycilic acid, niacinamide, magnesium carbonate hydroxide, cinnamon essential oil, cinnamon bark essential oil, cinnamic aldehyde, zinc oxide, or mixtures thereof.

4. The composition of claim 1, wherein the composition has a pH greater than about 9.0 at 60 minutes as measured by the pH Release Test Method.

5. The composition of claim 1, wherein the composition has a pH greater than about 9.5 at 60 minutes as measured by the pH Release Test Method.

6. The composition of claim 1, wherein the primary emollient is chosen from a silicone and/or a liquid triglyceride.

7. The composition of claim 1, wherein the at least one wax is chosen from an ester wax, ozokerite, paraffin wax, a fatty alcohol, or mixtures thereof.

8. The composition of claim 2, wherein the metal oxide is magnesium oxide.

9. The composition of claim 1, wherein the primary emollient is a liquid triglyceride, and wherein the liquid triglyceride is chosen from caprylic/capric triglyceride, triheptanoin, or mixtures thereof.

10. The composition of claim 1, wherein the primary emollient is a liquid triglyceride having a chain length from C8 to C10.

11. A homogeneous deodorant stick composition comprising:
    a. a metal oxide;
    b. a primary emollient chosen from a silicone and/or a liquid triglyceride; and
    c. at least one wax with a melting point above 50° C., chosen from an ester wax, ozokerite, paraffin wax, a fatty alcohol, or mixtures thereof;
    wherein the composition is anhydrous and aluminum-free;
    wherein the composition is free of calcium hydroxide;
    and wherein the composition has a pH greater than about 8.0 at 60 minutes as measured by the pH Release Test Method; and
    wherein the composition has a hardness penetration less than 200 mm*10 as measured by the Hardness Test Method.

12. The composition of claim 11, wherein the metal oxide is chosen from magnesium oxide, calcium oxide, or mixtures thereof.

13. The composition of claim 11, further comprising an additional antimicrobial chosen from piroctone olamine, beryllium carbonate, magnesium carbonate, calcium carbonate, magnesium hydroxide, magnesium hydroxide and magnesium carbonate hydroxide, partially carbonated magnesium hydroxide, piroctone olamine potassium carbonate, potassium bicarbonate, sodium carbonate, sodium sesquicarbonate, sodium bicarbonate, hexamidine, zinc carbonate, thymol, polyvinyl formate, salycilic acid, niacinamide, magnesium carbonate hydroxide, cinnamon essential oil, cinnamon bark essential oil, cinnamic aldehyde, zinc oxide or mixtures thereof.

14. The composition of claim 11, wherein the composition has a pH greater than about 9.0 at 60 minutes as measured by the pH Release Test Method.

15. The composition of claim 11, wherein the composition has a pH greater than about 9.5 at 60 minutes as measured by the pH Release Test Method.

16. The composition of claim 11, wherein the primary emollient is a liquid triglyceride having a chain length from C8 to C10.

17. The composition of claim 10, wherein the composition comprises at least about 20% by weight of the liquid triglyceride.

18. The composition of claim 16, wherein the composition comprises at least about 20% by weight of the liquid triglyceride.

* * * * *